United States Patent
Su et al.

(10) Patent No.: US 6,258,785 B1
(45) Date of Patent: Jul. 10, 2001

(54) CRYSTALLINE 9-E-(O-METHYL)OXIME OF 11, 12-DIDEOXY-3-DE(2,6-DIDEOXY-3-C-METHYL-3-O-METHYL-α-L-RIBOHEXOPYRANOSYLOXY)-6-O-METHYL-12,11-(IMINOCARBONYL-(2-(3-(4-(3-PYRIDINYL)1H-IMADAZOL-1-YL)PROPYL)HYDRAZONO))-3-OXOERYTHROMYCIN

(75) Inventors: Wei-Guo Su, East Lyme; Takushi Kaneko, Guilford; Yong-Jin Wu, Madison, all of CT (US); Daniel J. Durkin, San Francisco, CA (US); Kathleen T. Smyth, West Roxbury, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/449,136

(22) Filed: Nov. 24, 1999

Related U.S. Application Data

(60) Provisional application No. 60/110,543, filed on Dec. 2, 1998.

(51) Int. Cl.[7] .............................. A61K 31/70; C07H 17/08
(52) U.S. Cl. ................................................ 514/29; 536/7.4
(58) Field of Search ................................. 536/7.5; 514/29

(56) References Cited

U.S. PATENT DOCUMENTS 5,912,331 * 6/1999 Wilkening .............................. 536/7.5

FOREIGN PATENT DOCUMENTS

WO 98/56800   12/1999   (WO) .

* cited by examiner

*Primary Examiner*—Elli Peselev
(74) *Attorney, Agent, or Firm*—Peter C. Richardson; Paul H. Ginsburg; Bryan C. Zielinski

(57) ABSTRACT

The invention relates to crystalline 9-E-(O-methyl)oxime of 11,12-dideoxy-3-de(2,6-dideoxy-3-C-methyl-3-O-methyl-α-L-ribohexopyranosyloxy)-6-O-methyl-12,11-(iminocarbonyl-(2-(3-(4-(3-pyridinyl)-1H-imidazol-1-yl)propyl)hydrazono))-3-oxoerythromycin wherein said crystalline compound is as the free base of said compound, the hemihydrate of said compound or the mesylate (methanesufonic acid) salt of said compound. The invention also relates to pharmaceutical compositions containing the foregoing crystalline compound and to methods of treating bacterial and protozoa infections by administering said crystalline compound.

10 Claims, No Drawings

CRYSTALLINE 9-E-(O-METHYL)OXIME OF 11, 12-DIDEOXY-3-DE(2,6-DIDEOXY-3-C-METHYL-3-O-METHYL-α-L-RIBOHEXOPYRANOSYLOXY)-6-O-METHYL-12,11-(IMINOCARBONYL-(2-(3-(4-(3-PYRIDINYL)1H-IMADAZOL-1-YL)PROPYL) HYDRAZONO))-3-OXOERYTHROMYCIN

Priority is claimed from U.S. Provisional Patent Application Ser. No. 60/110,543, filed Dec. 2, 1998.

BACKGROUND OF THE INVENTION

This invention relates crystalline 9-E-(O-methyl)oxime of 11,12-dideoxy-3-de(2,6-dideoxy-3-C-methyl-3-O-methyl-α-L-ribohexopyranosyloxy)6-O-methyl-12,11 -(iminocarbonyl-(2-(3-(4-(3-pyridinyl)-1H-imidazol-1-yl) propyl)hydrazono))-3-oxoerythromycin wherein said crystalline compound is the free base of said compound (including the hemihydrate of said free base) or the mesylate (methanesulfonic acid) salt of said compound. The crystalline compound of this invention is useful as an antibiotic agent in mammals, including man, as well as in fish and birds. The compound of the present invention is a broad-spectrum macrolide antibiotic that is effective against infections caused by certain gram-positive and gram-negative bacteria as well as protozoa.

A non-crystalline, amorphous form of 9-E-(O-methyl) oxime of 11,12-dideoxy-3-de(2,6-dideoxy-3-C-methyl-3-O-methyl-α-L-ribohexopyranosyloxy)-6-O-methyl-12,11 -(iminocarbonyl-(2-(3-(4-(3-pyridinyl)-1H-imidazol-1-yl) propyl)hydrazono))-3-oxoerythromycin is referred to in PCT international patent application number PCT/IB98/00741, filed May 15, 1998, which is incorporated herein by reference in its entirety. The crystalline compound of the present invention is believed to be more stable than the amorphous compound referred to in the foregoing PCT application, which facilitates the manufacture of precise dosage forms of the compound for pharmaceutical use and improves the shelf-life of the compound. The crystallization of the amorphous compound significantly improves the purity of the compound which further facilitates the preparation of precise and safe dosage forms of the compound for pharmaceutical use. Further, the crystalline hemihydrate form of the free base is non-hygroscopic which is advantageous in the manufacture of accurate dosages.

SUMMARY OF THE INVENTION

The present invention relates to crystalline 9-E-(O-methyl)oxime of 11,12-dideoxy-3-de(2,6-dideoxy-3-C-methyl-3-O-methyl-α-L-ribohexopyranosyloxy)-6-O-methyl- 2,11 -(iminocarbonyl-(2-(3-(4-(3-pyridinyl)-1H-imidazol-1 -yl)propyl)hydrazono))-3-oxoerythromycin wherein said crystalline compound is either the free base of said compound (including the hemihydrate of said free base) or the methane sulfonic acid salt of said compound.

The invention also relates to a pharmaceutical composition for the treatment of a bacterial infection or a protozoa infection in a mammal, fish, or bird which comprises a therapeutically effective amount of the crystalline compound referred to above and a pharmaceutically acceptable carrier.

The invention also relates to a method of treating a bacterial infection or a protozoa infection in a mammal, fish, or bird which comprises administering to said mammal, fish or bird a therapeutically effective amount of the crystalline compound referred to above.

The present invention also relates to the preparation of crystalline 9-E-(O-methyl)oxime of 11,12-dideoxy-3-de(2, 6-dideoxy-3-C-methyl-3-0-methyl-α-L-ribohexopyranosyioxy)-6-0-methyl-12,11 -(iminocarbonyl-(2-(3-(4-(3-pyridinyl)-1H-imidazol-1 -yl)propyl) hydrazono))-3-oxoerythromycin (including the hemihydrate of said compound) which comprises introducing amorphous 9-E-(O-methyl)oxime of 11,12-dideoxy-3-de(2,6-dideoxy-3-C-methyl-3-O-methyl-α-L-ribohexopyranosyloxy)+O-methyl-12,11 -(iminocarbonyl-(2-(3-(4-(3-pyridinyl)-1H-imidazol-1 -yl)propyl)hydrazono))-3-oxoerythromycin into a solvent comprising $(C_1–C_6 \text{ alkyl})_2O_1$ such as isopropyl ether or methyl tert-butyl ether, containing ethanol, heating the composition to approximately 60° C., and then cooling the composition to a temperature within the range of about 20° C. to 25° C.

The present invention also relates to the preparation of crystalline 9-E-(O-methyl)oxime of 11,12-dideoxy-3-de(2, 6-dideoxy-3-C-methyl-3-O-methylα-L-ribohexopyranosyloxy)-6-O-methyl-12,11-(iminocarbonyl-(2-(3-(4-(3-pyridinyl)-1H-imidazol-1 -yl)propyl) hydrazono))-3-oxoerythromycin methanesulfonate which comprises treating a composition of amorphous 9-E-(O-methyl)oxime of 11,12-dideoxy-3-de(2,6-dideoxy-3-C-methyl-3-O-methyl-α-L-ribohexopyranosyloxy)-6-O-methyl-12,11 iminocarbonyl-(2-(3-(4-(3-pyridinyl)-1H-imidazol-1-yl)propyl)hydrazono))-3-oxoerythromycin in a polar organic solvent such as $CH_2Cl_2$, methanol, or ethanol, or a mixture of the foregoing solvents, preferably $CH_2Cl_2$, with methanesulfonic acid, evaporating the composition to provide a residue containing 9-E-(O-methyl)oxime of 11,12-dideoxy-3-de(2,6-dideoxy-3-C-methyl-3-0-methyl-α-L-(ibohexopyranosyloxy)-6-O-methyl-12,11-(iminocarbonyl-(2-(3-(4-(3-pyridinyl)-1H-imidazol-1-yl)propyl) hydrazono))-3-oxoerythromycin methanesulfonate, dissolving the residue in ethyl acetate, introducing isopropyl ether into the ethyl acetate composition, and then concentrating the resulting composition.

The term "treatment", as used herein, unless otherwise indicated, includes the treatment or prevention of a bacterial infection or protozoa infection as provided in the method of the present invention, including curing, reducing the symptoms of or slowing the progress of said infection. The terms "treat" and "treating" are defined in accord the foregoing term "treatment".

As used herein, unless otherwise indicated, the term "bacterial infection(s)" or "protozoa infection" includes bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus*,or *Peptostreptococcus* spp.; pharyngitis, rheumatic fever, and glomerulonephritis related to infection by *Streptococcus pyogenes*, Groups C and G *streptococci, Clostridium diptheriae,* or *Actinobacillus haemolyticum;* respiratory tract infections related to infection by *Mycoplasma pneumoniae, Legionella pneumophila, Streptococcus pneumoniae, Haemophilus influenzae,* or *Chlamydia pneumoniae;* uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *Streptococcus pyogenes, Streptococcus agalactiae*, Streptococcal groups C–F (minute- colony streptococci), viridans streptococci, *Corynebacterium minutissimum*, Clostridium spp., or *Bartonella henselae;* uncomplicated acute urinary tract infections related to infection by *Staphylococcus saprophyticus* or Enterococcus spp.; urethritis and cervicitis; and sexually transmitted diseases related to infection by *Chlamydia trachomatis, Haemophilus ducreyi, Treponema pallidum, Ureaplasma urealyticum,* or *Neisernia gonordieae;* toxin diseases related to infection by *S. aureus* (food poisoning and Toxic shock syndrome), or Groups A, B, and C streptococci; ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *Chlamydia trachomatis, Neisseria gonorrhoeae, S. aureus, S. pneumoniae, S. pyogenes, H. influenzae,* or Listeria spp.; disseminated *Mycobacterium avium* complex (MAC) disease related to infection by *Mycobacterium avium*, or *Mycobacterium intracellulare;* gastroenteritis related to infection by *Campylobacter jejuni;* intestinal protozoa related to infection by Cryptosporidium spp.; odontogenic infection related to infection by viridans streptococci; persistent cough related to infection by *Bordetella pertussis:* gas gangrene related to infection by *Clostridium perfringens* or Bacteroides spp.; and atherosclerosis related to infection by *Helicobacter pylod* or *Chlamydia pneumoniae*. Bacterial infections and protozoa infections and disorders related to such infections that may be treated or prevented in animals include the following: bovine respiratory disease related to infection by *P. haem., P. multocida, Mycoplasma bovis,* or Bordetella spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae, Klebsiella* spp., Corynebactedum, or Enterococcus spp.; swine respiratory disease related to infection by *A. pleuro., P. multocida,* or Mycoplasma spp.; swine enteric disease related to infection by *E. coli, Lawsonia intracelluladis, Salmonella,* or *Serpulina hyodyisinteriae;* cow footrot related to infection by Fusobacterium spp.; cow metritis related to infection by *E. coli,* cow hairy warts related to infection by *Fusobacterium necrophorum* or *Bacteroides nodosus;* cow pink-eye related to infection by *Moraxella bovis;* cow premature abortion related to infection by protozoa (i.e. neosporium); urinary tract infection in dogs and cats related to infection by *E. coli;* skin and soft tissue infections in dogs and cats related to infection by *Staph. epidermidis, Staph. intermedius,* coagulase neg. Staph. or *P. multocida;* and dental or mouth infections in dogs and cats related to infection by *Alcaligenes* spp., Bactemoides spp., Clostridium spp., Enterobacter spp., Eubacterium, Peptostreptococcus, Porphyromonas, or Prevotella. Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

The present invention also includes all radiolabelled forms of the crystalline compounds of the present invention wherein the radiolabel is selected from $^3$H, $^{11}$C and $^{14}$C. Such radiolabelled compounds are useful as research or diagnostic tools.

DETAILED DESCRIPTION OF THE INVENTION

The crystalline compounds of the present invention may be prepared using amorphous 9-E-(O-Methyl)oxime of 11,12-Dideoxy-3-de(2,6-dideoxy-3-C-methyl-3-O-methyl-α-L-ribohexopyranosyloxy)-6-O-methyl-12,11-(iminocarbonyl-(2-(3-(4-(3-pyridinyl)-1H-imidazol-1-yl)propyl)hydrazono))-3-oxoerythromycin (hereinafter "amorphous compound") as starting material which may be prepared as described in PCT/IB98/00741, referred to above. The free base form of the crystalline compounds of the present invention may be prepared by suspending the amorphous compound in isopropyl ether containing approximately 3% ethanol and heating the suspension to approximately 60° C. for approximately 24 hours and then stirring the mixture for an additional period of approximately 3 days at room temperature (about 20–25° C.). The mesylate salt of the crystalline compounds of the present invention may be prepared by treating a solution of the amorphous compound in $CH_2Cl_2$ with methane-sulfonic acid in $CH_2Cl_2$, and stirring the resulting mixture for approximately 15 minutes at room temperature (about 20–25° C.) and then evaporating the solvent to provide a residue. The residue is first dissolved in ethyl acetate and then isopropyl ether is added to this solution. Crystals of the mesylate salt of 9-E-(O- Methyl) oxime of 11,12-Dideoxy-3-de(2,6-dideoxy-3-C-methyl-3-O-methyl-α-L- ribohexopyranosyloxy)6-O-methyl-12,11-(iminocarbonyl-(2-(3-(4-(3-pyridinyl)-1H-imidazol-1 -yl)propyl)hydrazono))-3-oxoerythromycin will form upon concentration of the solution and then letting the solution stand at room temperature overnight.

The activity of the crystalline compounds of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to effiux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The assay is performed in microtiter trays and interpreted according to *Performance Standards for Antimicrobial Disk Susceptibility Tests-Sixth Edition: Approved Standard*, published by The National Committee for Clinical Laboratory Standards (NCCLS) guidelines; the minimum inhibitory concentration (MIC) is used to compare strains. The crystalline compound is initially dissolved in dimethylsulfoxide (DMSO) as 40 mg/ml stock solution.

| Strain Designation | Macrolide Resistance Mechanism(s) |
|---|---|
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | ermB |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Streptococcus pneumoniae* 0085 | susceptible |
| *Haemophilus influenzae* 0131 | susceptible |
| *Moraxella catarrhalis* 0040 | susceptible |
| *Moraxella catarrhalis* 1055 | erythromycin intermediate resistance |
| *Escherichia coli* 0266 | susceptible |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The test compound is prepared by solubilizing 1 mg of the compound in 125 $\mu$l of dimethylsulfoxide (DMSO). Dilutons of the test compound are prepared using uninoculated BHI broth. The concentrations of the test compound used range from 200 $\mu$g/ml to 0.098 $\mu$g/ml by two-fold serial dilutions. The *P. multocida* inoculated BHI is diluted with uninoculated BHI broth to make a $10^4$ cell suspension per 200 $\mu$l. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 $\mu$l of the fully grown P. haemolytica preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 $\mu$l of the *P. haemolytica* culture is inoculated onto BHI agar plates containing the various concentrations of the test compound using a Steers Replicator and incubated for 18 hours at 37° C. Initial concentrations of the test compound range from 100–200 $\mu$g/ml. The MIC is equal to the concentration of the test compound exhibiting 100% inhibition of growth of *P. haemolytica* as determined by comparison with an uninoculated control.

The in vivo activity of the crystalline compound of the present invention can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3\times10^3$ CFU/ml bacterial suspension (*P. multocida* strain 59A006) intraperitoneally. Each experiment has at least 3 non-medicated control groups including one infected with 0.1X challenge dose and two infected with 1X challenge dose; a 10X challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment.

The crystalline compounds of the present invention (hereinafter "the active compound"), may be adminstered through oral, parenteral, topical, or rectal routes in the treatment or prevention of bacterial or protozoa infections. In general, these active compound is most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compound may be administered alone or in combination with pharmaceutically acceptable carriers or diluents by the routes previously indicated, and such administration may be carried out in single or multiple doses. More particularly, the active compound may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compound are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of the active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compound topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compound may also be adminstered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compound may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compound may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The Examples provided below illustrate specific embodiments of the invention, but the invention is not limited in scope to the Examples specifically exemplified.

EXAMPLE 1

Preparation of Crystalline 9-E-(O-Methyl)oxime of 11,12-Dideoxy-3-de(2.6-dideoxy-3-C-methyl-3-O-methyl-α-L-ribohexopyranosyloxy)-6-O-methyl-12, 11 -(iminocarbonyl-(2-(3-(4-(3-pyridinyl)-1H-imidazol-1-yl)propyl)hydrazono))-3-oxoerythromycin hemihydrate Amorphous 9-E-(O-methyl)oxime of 11,12-dideoxy-3-de (2,6-dideoxy-3-C-methyl-3-O-methyl-α-L-ribohexopyranosyloxy)-6-O-methyl-12,11-(iminocarbonyl-(2-(3-(4-(3-pyridinyl)-1H-imidazol-1-yl)propyl) hydrazono))-3-oxoerythromycin (130 g) was suspended in 3L of isopropyl ether containing 3% ethanol. The suspension was heated to 60° C. overnight and stirring was continued at room temperature (about 20–25° C.) for an additional 3 days. The resulting solid was collected by filtration to give 81 g of the title compound; mp 177° C. The water solubility of the resulting crystals was greater than 11 mg/ml in phosphate buffer solution (pH 6.5) at room temperature. The crystals were characterized by the powder X-ray diffraction pattern noted below.

Characteristics of peaks found in X-ray diffraction pattern for crystalline 9-E-(O-methyl)oxime of 11,12-dideoxy-3-de (2,6-dideoxy-3-C-methyl-3-O-methyl-α-L-ribohexopyranosyloxy)-6-O-methyl-12,11 -(iminocarbonyl-(2-(3-(4-(3-pyridinyl)-1H-imidazol-1-yl)propyl) hydrazono))-3-oxoerythromycin hemihydrate.

| Peak No. | 1 | 2 | 3 | 4 | 5 |
|---|---|---|---|---|---|
| 2q (°) Cu | 7.9 | 9.6 | 10.6 | 13.2 | 14.1 |
| d space | 11.2 | 9.2 | 8.3 | 6.7 | 6.3 |
| Peak No. | 6 | 7 | 8 | 9 | 10 |
| 2q (°) Cu | 17.4 | 17.9 | 18.3 | 19.5 | 21.1 |
| d space | 5.1 | 5.0 | 4.8 | 4.6 | 4.2 |

EXAMPLE 2

Preparation of Methanesulfonic Acid Salt of 9-E-(O-Methyl)oxime of 11,12-dideoxy-3-de(2,6-dideoxy-3-C-methyl-3-O-methyl-α-L-ribohexopyranosyloxy)-6-O-methyl-12,11-(iminocarboxyl-(2-(3-(4-(3-pyridinyl)-1H-imidazol-1-yl)-propyl)hydrazo))-3-oxoerythromycin To a solution of amorphous 9-E-(O-methyl)oxime of 11,12-dideoxy-3-de(2,6-dideoxy-3-C-methyl-3-O-methyl-α-L-ribohexopyranosyloxy)-6-O-methyl-12,11-(iminocarbonyl-(2-(3-(4-(3-pyridinyl)-1H-imidazol-1-yl)

propyl)hydrazono))-3-oxoerythromycin (200 mg) in 3 mL of $CH_2Cl_2$ was added 1.19 mL of 2M solution of methanesulfonic acid in $CH_2Cl_2$. The solution was stirred at room temperature (about 20–25° C.) for 15 minutes, and the solvent was evaporated. The residue was dissolved in 2 mL of ethyl acetate, and to this solution was added 1 mL of isopropyl ether. The solution was concentrated to approximately 0.5 mL and was left standing at room temperature (about 20–25° C.). The resulting crystals were collected by filtration to 175 mg of the title compound; mp: 193–194° C. The water solubility of the resulting crystals was 24 mg/ml in phosphate buffer solution (pH 6.5). The crystals were characterized by the powder x-ray diffraction pattern noted below.

Characteristics of peaks found in X-ray diffraction pattern of the crystalline methanesulfonic acid salt of 9-E-(O-methyl)oxime of 11,12-dideoxy-3-de(2,6-dideoxy-3-C-methyl-3-O-methyl-α-L-ribohexopyranosyloxy)6-O-methyl-12,11 -(iminocarbonyl-(2-(3-(4-(3-pyridinyl)-1H-imidazol-1-yl)propyl)hydrazono))-3-oxoerythromycin.

| Peak No. | 1 | 2 | 3 | 4 | 5 |
|---|---|---|---|---|---|
| 2q (°) Cu | 7.9 | 9.6 | 10.6 | 11.6 | 12.8 |
| d space | 11.2 | 9.2 | 8.3 | 7.6 | 6.9 |
| Peak No. | 6 | 7 | 8 | 9 | 10 |
| 2q (°) Cu | 13.2 | 14.2 | 18.0 | 20.0 | 21.3 |
| d space | 6.7 | 6.2 | 4.9 | 4.5 | 4.2 |

The E-configuration of the oxime moiety of 9-E-(O-methyl)oxime of 11,12-dideoxy-3-de(2,6-dideoxy-3-C-methyl-3-1-methyl-α-L-ribohexopyranosyloxy)-6-O-methyl-12,1-(iminocarbonyl-(2-(3-(4-(3-pyridinyl)-1H-imidazol-1-yl)propyl)hydrazono))-3-oxoerythromycin was confirmed by dissolving the compound in methanol (4.2 ml) at room temperature. The solution was diluted with isopropyl ether and heated at reflux on a hot plate until cloudy (120 ml of isopropyl ether used). The resulting solution was let stand at room temperature for one week. Crystals were collected by filtration, washed with 10:1 isopropyl ether-methanol and dried under air to yield 1.2 g of crystalline pellets. A single crystal X-ray crystallography was performed, according to standard methods familiar to those skilled in the art, which confirmed that the oxime moiety at C-9 of the macrolide ring has the E-configuration.

What is claimed is:

1. Crystalline 9-E-(O-methyl)oxime of 11,12-dideoxy-3-de(2,6-dideoxy-3-C-methyl-3-O-methyl-α-L-ribohexopyranosyloxy)-6-O-methyl-12,11-(iminocarbonyl-(2-(3-(4-(3-pyridinyl)-1H-imidazol-1-yl)propyl)hydrazono))-3-oxoerythromycin wherein said crystalline compound is the free base of said compound, the hemihydrate of said compound, or the methanesulfonic acid salt of said compound.

2. A compound according to claim 1 wherein said compound is the free base of said crystalline compound.

3. A compound according to claim 2 wherein said compound is the hemihydrate form of said compound.

4. A compound according to claim 1 wherein said compound is the methanesulfonic acid salt of said crystalline compound.

5. A pharmaceutical composition for the treatment of a bacterial infection or a protozoa infection in a mammal, fish or bird which comprises a therapeutically effective amount of a compound of claim 1 and a pharmaceutically acceptable carrier.

6. A method of treating a bacterial infection or a protozoa infection in a mammal, fish, or bird which comprises administering to said mammal, fish, or bird a therapeutically effective amount of a compound of claim 1.

7. A method of preparing crystalline 9-E-(O-methyl) oxime of 11,12-dideoxy-3-de(2,6-dideoxy-3-C-methyl-3methyl-α-L-ribohexopyranosyloxy)-6-O-methyl-12,11-(iminocarbonyl-(2-(3-(4-(3-pyridinyl)-1H-imidazol-1 -yl) propyl)hydrazono))-3-oxoerythromycin which comprises introducing amorphous 9-E-(O-methyl)oxime of 11,12-dideoxy-3-de(2,6-dideoxy-3-C-methyl-3-O-methyl-α-L-ribohexopyranosyloxy)-6-O-methyl-12,11-(iminocarbonyl-(2-(3-(4-(3-pyridinyl)-1H-imidazol-1-yl)propyl) hydrazono))-3-oxoerythromycin into a solvent comprising $(C_1–C_6$ alkyl$)_2$O containing ethanol, heating the composition to approximately 60° C., and cooling the composition to a temperature within the range of about 20° C. to 25° C.

8. A method according to claim 7 wherein said solvent comprises isopropyl ether containing ethanol or methyl tert-butyl ether containing ethanol.

9. A method of preparing crystalline 9-E-(O-methyl) oxime of 11,12-dideoxy-3-de(2,6-dideoxy-3-C-methyl-3-O-methyl-α-L-ribohexopyranosyloxy)-O-methyl-12,11-(iminocarbonyl-(2-(3-(4-(3-pyridinyl)-1H-imidazol-1-yl) propyl)hydrazono))-3oxoerythromycin methanesulfonate which comprises treating a composition of amorphous 9-E-(O-methyl)oxime of 11,12-dideoxy-3-de(2,6-dideoxy-3-C-methyl-3-O-methyl-α-L-ribohexopyranosyloxy)6-O-methyl-12,11-(iminocarbonyl-(2-(3-(4-(3-pyridinyl)-1H-imidazol-1-yl)propyl)hydrazono))-3-oxoerythromycin in a polar organic solvent with methanesulfonic acid, evaporating the composition to provide a residue containing 9-E-(O-methyl)oxime of 11,12-dideoxy-3-de(2,6-dideoxy-3-C-methyl-3-O-methyl-α-L-ribohexopyranosyloxy)6-O-methyl-12,11-(iminocarbonyl-(2-(3-(4-(3-pyridinyl)-1H-imidazol-1-yl)propyl)hydrazono))-3-oxoerythromycin methanesulfonate, dissolving the residue in ethyl acetate, introducing isopropyl ether into the ethyl acetate composition, and concentrating the resulting composition.

10. A method according to claim 9 wherein said polar organic solvent comprises $CH_2Cl_2$, methanol, or ethanol, or a mixture of the foregoing solvents.

* * * * *